US00PP14226P39

(12) United States Plant Patent
Brea

(10) Patent No.: US PP14,226 P3
(45) Date of Patent: Oct. 14, 2003

(54) ROSE PLANT NAMED 'BREAPUM'

(50) Latin Name: *Rosa hybrida*
Varietal Denomination: Breapum

(75) Inventor: Ezio Brea, San Remo (IT)

(73) Assignee: Azienda Agricola Brea Ezio, San Remo (IT)

( * ) Notice: Subject to any disclaimer, the term of this patent is extended or adjusted under 35 U.S.C. 154(b) by 0 days.

(21) Appl. No.: 09/887,000

(22) Filed: Jun. 25, 2001

(65) Prior Publication Data

US 2002/0199223 P1 Dec. 26, 2002

(51) Int. Cl.[7] ..... A01H 5/00

(52) U.S. Cl. ..... Plt./110

(58) Field of Search ..... Plt./101, 102, 103, Plt./109, 110, 111

(56) References Cited

PUBLICATIONS

UPOV–ROM, 2001/04, Plant Variety Database, GTI Jouve Retrieval Software, citation for 'Breapum', 2001.*

* cited by examiner

*Primary Examiner*—Howard J. Locker
(74) *Attorney, Agent, or Firm*—C. A. Whealy

(57) ABSTRACT

A new and distinct cultivar of Rose plant named 'Breapum', characterized by its long erect flowering stems; creamy white-colored flowers; and unique orange-colored hips arranged in sprays.

1 Drawing Sheet

Botanical classification: *Rosa hybrida* cultivar Breapum.

BACKGROUND OF THE INVENTION

The present Invention relates to a new and distinct cultivar of Rose plant, botanically known as *Rosa hybrida,* commercially used as a rambler cut Rose stem with hips, and hereinafter referred to by the name 'Breapum'.

The new Rose is a product of a planned breeding program conducted by the Inventor in San Remo, Italy. The objective of the breeding program was to develop new cut Rose cultivars with unique and attractive hip color.

The new Rose originated from a cross made by the Inventor in San Remo, Italy of a proprietary selection of *Rosa hybrida* identified as code number BR 103, not patented, as the female, or seed, parent and a proprietary selection of *Rosa hybrida* identified as code number BR 54, not patented, as the male, or pollen, parent. The new Rose was discovered and selected by the Inventor in 1995 as a flowering plant within the progeny of the stated cross in a controlled environment in San Remo, Italy. The selection of this new Rose was based on its unique orange hip color.

Asexual reproduction of the new cultivar by cuttings taken at San Remo, Italy since 1996, has shown that the unique features of this new Rose are stable and reproduced true to type in successive generations.

SUMMARY OF THE INVENTION

Plants of the cultivar Breapum have not been observed under all possible environmental conditions. The phenotype may vary somewhat with variations in environment such as temperature, light intensity, daylength, water status, and fertilizer type or rate without, however, any variance in genotype.

The following traits have been repeatedly observed and are determined to be the unique characteristics of 'Breapum'. These characteristics in combination distinguish 'Breapum' as a new and distinct cultivar:

1. Long erect flowering stems.
2. Creamy white-colored flowers.
3. Orange-colored hips arranged in sprays.

Plants of the new Rose differ primarily from plants of the parent selections in rose hip color as plants of the parent selections have red-colored hips.

In side-by-side comparisons conducted in Aalsmeer, The Netherlands, plants of the new Rose differ from plants of the cultivar Bapollu, disclosed in U.S. Plant Pat. No. 12,483, primarily in hip coloration as plants of the cultivar Bapollu have dark red-colored hips.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Rose. The photograph comprises a side perspective view of a typical flowering stem of 'Breapum' with developing hips.

DETAILED BOTANICAL DESCRIPTION

The following observations, measurements and values describe plants of the new cultivar grown in Aalsmeer, The Netherlands in an outdoor nursery. During the production of the plants, day temperatures ranged from 0 to 30° C. and night temperatures ranged from −5 to 19° C. Plants used for the photograph and description were about 6 months from planting rooted cuttings. Color references are made to The Royal Horticultural Society Colour Chart except where general terms of ordinary dictionary significance are used.

Classification:

*Botanical.*—*Rosa hybrida* cultivar Breapum.

*Commercial.*—Cut Rose stem with orange-colored hips.

Parentage:

*Female parent.*—Proprietary selection of *Rosa hybrida* identified as code number BR 103, not patented.

*Male parent.*—Proprietary selection of *Rosa hybrida* identified as code number BR 54, not patented.

Propagation:

*Type.*—By cuttings.

*Time to initiate and develop roots.*—Summer: About 14 days at 23° C. Winter: About 21 days at 23° C.

*Root description.*—Fine, fibrous.

*Rooting habit.*—Freely branching.

Plant description:

*Form.*—Upright, tall, columnar.

*Vigor.*—Vigorous.

*Crop time.*—Rapid growth rate, from rooted cuttings, about 6 months are required to produce stems with fully developed hips.

*Flowering stem description.*—Quantity: About seven flowering stems per plant. Aspect: Erect. Length: Long, more than 1.5 m. Spread: About 50 cm. Diameter: About 1 cm. Strength: Very strong, rigid. Texture: Smooth, glabrous; numerous red-colored thorns. Color: 138A. Thorns: Quantity: About 80 to 100 per stem. Length: About 1 cm. Diameter at base: About 1 cm. Color: 60C.

*Foliage description.*—Leaves compound with five to seven leaflets; alternate, generally symmetrical, durable and long persisting. Quantity per flowering stem: About 40. Length: Entire compound leaf: About 10 cm. Terminal leaflet: About 3 cm. Width: Entire compound leaf: About 6 cm. Terminal leaflet: About 2.5 cm. Shape: Ovate. Apex: Acute to acuminate. Base: Obtuse. Margin: Serrate. Texture, both surfaces: Smooth, glabrous. Venation pattern: Pinnate. Color: Young foliage, upper surface: 136B. Young foliage, lower surface: 59B. Mature foliage, upper surface: 137A. Mature foliage, lower surface: 137C. Rachis color: Close to 144C. Stipule: Shape: Lanceolate. Size: About 5 by 15 mm. Color: 144C.

Flower description:

*Flower type and habit.*—Single rounded flowers arranged in panicles. Overall shape of spray formation is globular to pyramidal. Freely and continuously flowering. Flowers persistent. Typically about 30 flowers per spray

*Natural flowering season.*—Flowering continuous throughout the summer in The Netherlands.

*Fragrance.*—Slight, typical of Rosa.

*Flower longevity on the plant.*—About 14 days.

*Flower longevity as a cut flower.*—About five to seven days.

*Flower diameter.*—About 6 cm.

*Flower depth.*—About 3 cm.

*Petals.*—Quantity: About 10 per flower in two whorls. Length: About 3 cm. Width: About 3.5 cm. Shape: Cordate. Apex: Emarginate. Margin: Entire, ruffled. Texture: Smooth, glabrous. Color: When opening and fully opened, upper surface: 158C; fading to 158D with subsequent development. When opening and fully opened, lower surface: 158C.

*Sepals.*—Quantity: Five per flower. Shape: Lanceolate; apex, acute; reflexing with development. Color upper and lower surfaces: Close to 137A.

*Pedicels.*—Angle: About 45° from stem. Strength: Strong. Length: About 4 cm. Diameter: About 2 mm. Color: 138A.

*Fruit* (*hips*).—Quantity per spray: About 30. Length: About 2 cm. Diameter: About 1.5 cm. Shape: Roughly spherical. Texture: Smooth. Color: When developing, light orange with green overtones; when fully developed, 31A. Days to ripening: About 80. Postproduction longevity as a cut stem: More than 30 days.

*Seed.*—Quantity: About 20 per fruit. Length: About 5 mm. Diameter: About 5 mm. Color: Light yellow.

*Reproductive organs.*—Many yellow-colored stamens and anthers, typical of species. Pistil color: 11C. Stamen color: 11C. Pollen amount: Abundant. Pollen color: 15C.

Disease tolerance: Plants of the new Rose has been observed to be tolerant to Powdery Mildew.

It is claimed:

1. A new and distinct cultivar of Rose plant named 'Breapum', as illustrated and described.

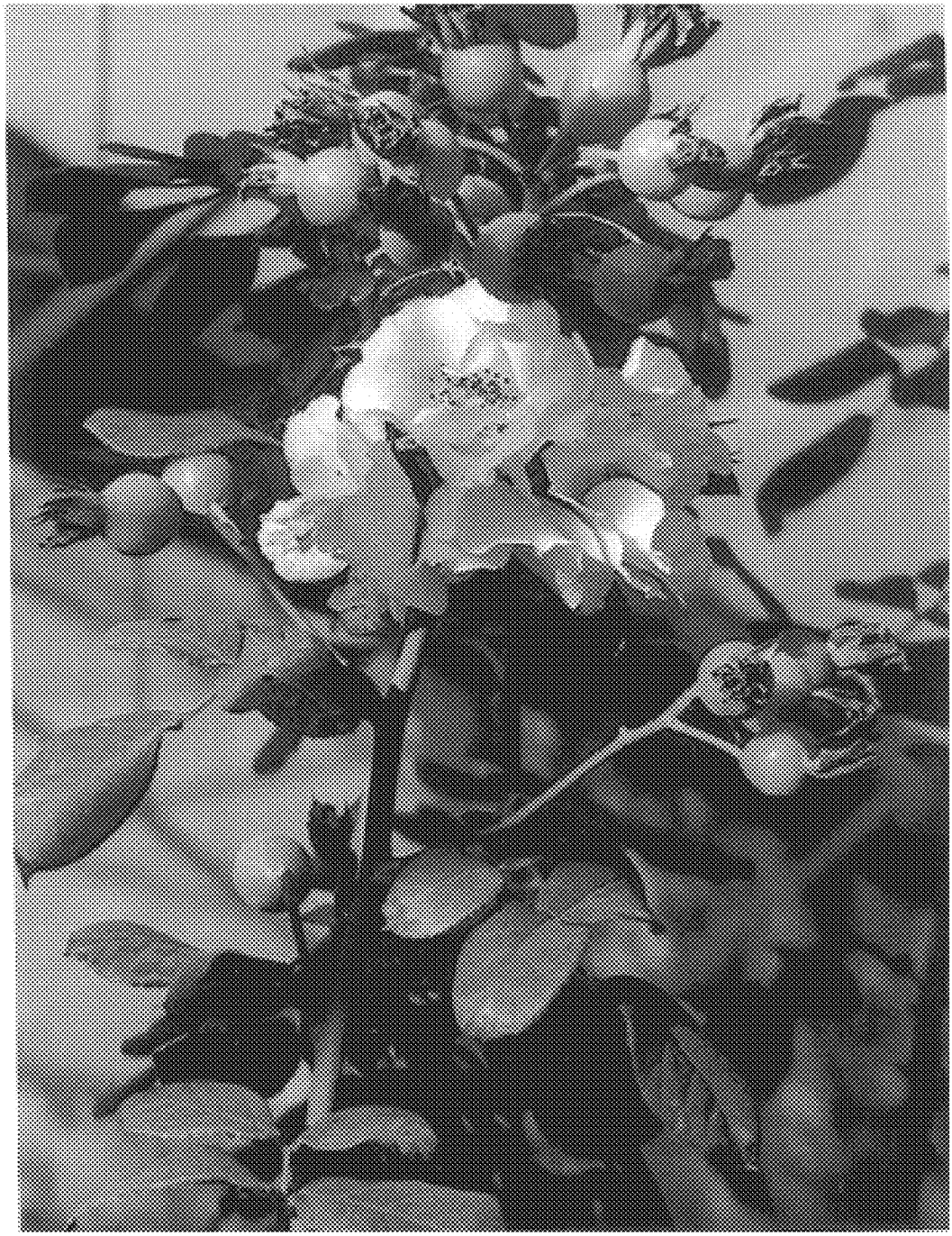

* * * * *